United States Patent
Tannoudji et al.

(10) Patent No.: US 10,416,451 B2
(45) Date of Patent: Sep. 17, 2019

(54) METHOD OF CONTROLLING A HEAD MOUNTED ELECTRO-OPTICAL DEVICE ADAPTED TO A WEARER

(71) Applicant: Essilor International, Charenton-le-Pont (FR)

(72) Inventors: Denis Cohen Tannoudji, Paris (FR); Antoine Videmann, Paris (FR); Amandine Debieuvre, Paris (FR); Marion Swital, Paris (FR); Benoit Callier, Paris (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 14/786,737

(22) PCT Filed: Apr. 25, 2014

(86) PCT No.: PCT/EP2014/058434
§ 371 (c)(1),
(2) Date: Oct. 23, 2015

(87) PCT Pub. No.: WO2014/174067
PCT Pub. Date: Oct. 30, 2014

(65) Prior Publication Data
US 2016/0070105 A1    Mar. 10, 2016

(30) Foreign Application Priority Data
Apr. 25, 2013    (EP) .................................. 13305542

(51) Int. Cl.
*G02B 27/01*    (2006.01)
*G06F 3/01*    (2006.01)
(Continued)

(52) U.S. Cl.
CPC ..... *G02B 27/0172* (2013.01); *G02B 27/0093* (2013.01); *G02B 27/017* (2013.01);
(Continued)

(58) Field of Classification Search
CPC .......... G06F 3/011; G06F 3/012; G06F 3/013; G02F 2203/69
See application file for complete search history.

(56) References Cited

U.S. PATENT DOCUMENTS 4,106,217 A    8/1978    Witt
4,601,545 A *  7/1986    Kern .................. G02B 26/0875
                                                    349/139
(Continued)

FOREIGN PATENT DOCUMENTS

WO    2001/02895 A1    1/2001
WO    WO 2011/106798 A1    9/2011
(Continued)

OTHER PUBLICATIONS

International Search Report and Written Opinion dated Aug. 20, 2014; PCT International Application No. PCT/EP2014/058434.
(Continued)

*Primary Examiner* — William Lu
(74) *Attorney, Agent, or Firm* — Oblon, McClelland, Maier & Neustadt, L.L.P.

(57) ABSTRACT

A method of controlling a head mounted see-through electro-optical device adapted to a wearer A method of controlling a head mounted electro-optical device adapted to a wearer, the method comprising: a wearer visual profile parameter providing step, during which the value of at least one wearer parameter related to the visual profile of the wearer is provided, an head mounted device function adapting step, during which the head mounted device function of
(Continued)

the electro-optical device is adapted based on the value of the at least one wearer parameter.

13 Claims, 1 Drawing Sheet

(51) Int. Cl.
    *G02C 7/10*     (2006.01)
    *G02B 27/00*     (2006.01)
    *A61F 9/02*     (2006.01)
    *G02C 7/06*     (2006.01)

(52) U.S. Cl.
    CPC .............. *G02C 7/101* (2013.01); *A61F 9/023* (2013.01); *G02B 2027/014* (2013.01); *G02B 2027/0118* (2013.01); *G02B 2027/0178* (2013.01); *G02B 2027/0181* (2013.01); *G02C 7/06* (2013.01); *G02C 2202/24* (2013.01)

(56) References Cited

U.S. PATENT DOCUMENTS

| | | | | |
|---|---|---|---|---|
| 5,444,559 | A * | 8/1995 | Warnar | G02F 1/13318 349/116 |
| 6,517,203 | B1 * | 2/2003 | Blum | C07K 14/5443 351/159.39 |
| 8,384,002 | B2 * | 2/2013 | Holladay | A61F 2/1618 250/201.2 |
| 9,046,730 | B2 * | 6/2015 | Li | G02F 1/13718 |
| 9,869,886 | B2 * | 1/2018 | Fleury | B60J 3/04 |
| 2005/0001155 | A1 * | 1/2005 | Fergason | B23K 9/32 250/221 |
| 2008/0151175 | A1 * | 6/2008 | Gross | G02C 7/086 351/45 |
| 2009/0213282 | A1 * | 8/2009 | Burlingame | G02C 7/101 349/13 |
| 2009/0279050 | A1 * | 11/2009 | McGinn | G02C 7/061 351/159.47 |
| 2011/0214082 | A1 * | 9/2011 | Osterhout | G02B 27/017 715/773 |
| 2012/0194781 | A1 * | 8/2012 | Agurok | A61B 3/113 351/201 |
| 2012/0212414 | A1 * | 8/2012 | Osterhout | G02B 27/017 345/158 |
| 2014/0184775 | A1 * | 7/2014 | Drake | A61B 3/14 348/78 |
| 2015/0185503 | A1 * | 7/2015 | Tate | G06F 3/013 351/158 |
| 2017/0123234 | A1 * | 5/2017 | Sabovic | G02C 7/083 |

FOREIGN PATENT DOCUMENTS

| | | |
|---|---|---|
| WO | 2012/036638 | 3/2012 |
| WO | 2012/037290 A2 | 3/2012 |

OTHER PUBLICATIONS

International Search Report and Written Opinion dated Jul. 4, 2014; PCT International Application No. PCT/EP2014/058434.

Office Action dated Jan. 8, 2019, in Japanese Patent Application No. 2016-509485 (with Unedited Computer-generated English translation), 7 pgs.

* cited by examiner

METHOD OF CONTROLLING A HEAD MOUNTED ELECTRO-OPTICAL DEVICE ADAPTED TO A WEARER

The invention relates to a method of controlling a head mounted electro-optical device adapted to a wearer, a computer program product and an electro-optical device adapted to implement the method of the invention.

The discussion of the background of the invention herein is included to explain the context of the invention. This is not to be taken as an admission that any of the material referred to was published, known or part of the common general knowledge at the priority date of any of the claims.

Head mounted electro-optical devices comprise at least a controllable electro-optical component which adjusts the head mounted device function of such devices.

Head mounted electro-optical devices may be composed of at least one see-through electro-optical component through which the user may see the real-world scene.

The control of the head mounted device function of such device may be used in a static manner, i.e. to set the head mounted device function of the device or in a dynamic manner, i.e. to adjust the head mounted device function of the device. In the dynamic mode, the head mounted device function of the prior art devices is adjusted based on changes in the environment of the wearer. For example, upon a detection of a change in luminosity of the environment the head mounted device function of the device may be adapted.

Among the head mounted see-through electro-optical devices, the head mounted display devices allow the user to observe the physical world around him or her, while optical elements add light from one or two small micro-displays into the user's visual path, to provide an augmented reality image. The augmented reality image may relate to a real-world scene which represents an environment in which a user is located.

Such head-mounted display devices are used in various applications, for example aviation, medicine, video gaming, entertainment, sports, and so forth.

The head mounted device function, in particular the transmission value of the see-through element may be adapted based on the luminosity of the environment so as to increase the contrast between the augmented reality image and the real-world scene. The features of the displayed augmented reality image may also be adapted, for example according to the luminosity of the environment.

Such prior art device adapted the head mounted device function based on an environment parameter, for example the environment luminosity. However, each wearer may have a different reaction to a change in the environment. For example each wearer does not have the same sensitivity to light intensity. The prior art devices are not adapted to take in consideration wearer parameters when dynamically adjusting the head mounted device function.

Therefore, there is a need for a method for controlling statically or dynamically the head mounted device function of a head mounted electro-optical device that is adapted to a wearer.

Furthermore, there is a need for a method for controlling statically or dynamically the head mounted device function of a head mounted electro-optical device to provide optimal visual comfort for the wearer.

A goal of the present invention is to provide such a method.

To this end, the invention proposes a method, for example implemented by computer means, of controlling a head mounted electro-optical device adapted to a wearer, the method comprising:
- a wearer visual profile parameter providing step S1, during which the value of at least one wearer parameter related to the visual profile of the wearer is provided,
- an head mounted device function adapting step S2, during which the head mounted device function of the electro-optical device is adapted based on the value of the at least one wearer parameter.

Advantageously, the method according to the invention allows a personalized adaptation of the head mounted device function of the head mounted electro-optical device. Indeed, according to the method of the invention, the head mounted device function is adapted based not only on an environment parameter but also based on a wearer parameter.

According to further embodiments which can be considered alone or in any possible combination:
- the method further comprises an environment parameter providing step, during which the value of at least one environment parameter relating to the environment of the wearer is provided; and/or
- at least one environment parameter relates to the status of the head mounted electro-optical device; and/or
- during the head mounted device function adapting step, the head mounted device function is switched between at least two predetermined head mounted device functions; and/or
- the head mounted electro-optical device comprises:
  - an optical lens,
  - at least an controllable light filter adapted to filter at least part of the light passing through the optical lens or reflected on the optical lens,
  - at least a light intensity sensor adapted to determine the light intensity of at least part of the wearer's environment,
  - a control unit configured to control the filter, and
  wherein the at least one wearer parameter relates to at least the light sensitivity of the wearer, the at least one visual parameter relates to at least the light intensity of at least part of the wearer's environment and during the head mounted device function adapting step at least the opacity of the filter is adapted; and/or
- at least one wearer parameter relates to the wearer's glare sensitivity and/or the wearer's eye color and/or the wearer's preference and/or the dilatation of the wearer's pupil and/or the wearer's blinking frequency and/or the wearer's squinting; and/or
- the head mounted electro-optical device further comprises a light emitting component, the controllable filter being placed between the environment and the light emitting component and/or between the wearer and the light emitting component when the device is worn by the user, and
- the method further comprises, prior to the light function adapting step, a filtration specification and level determining step during which at least a filtration level corresponding to a compromise between the light intensity of the emitter and the light of the controllable filter is determined according at least to the light intensity of at least part of the wearer's environment and at least a wearer parameter relating at least to the wearer's light sensitivity, and
- during the head mounted device function adapting step the light function of the filter is adapted based on the filtration specification and level determined during the filtration specification and level determining step; and/or the light emitting component comprises a display emitter adapted to emit light to the user's eye, the light representing an image or/and a letter, and during the head mounted device function adapting step, the filtration specification and level describe a static or dynamic pattern having a higher or lower filtration level within the surrounding of the display emitted light than the display area or some sub-part of the display area; and/or the head mounted electro-optical device is a see-through head mounted electro-optical device comprising:

an optical lens mounted to a frame worn by the wearer, the optical lens comprises at least a first and a second distinct vision zone, the first vision zone being adapted to a first distance vision, and the second vision zone being adapted for a second distance vision different from the first distance vision, an eye tracking component adapted to determine the gazing direction of the wearer, and wherein during the visual environment parameter providing step, at least one visual parameter relating to the viewing distance of the wearer is provided and at least one visual parameter relating to the gazing direction of the wearer is provided, during the light function adapting step, the light function is adapted so as to address a visual signal to the wearer when the gazing direction does not correspond to the viewing distance; and/or the viewing distance of the wearer is determined by comparing the gazing directions of both eyes of the wearer; and/or the visual signal address to the wearer comprises a change of color and/or of opacity of at least part of the electro-optical device and/or displaying a light to the wearer using a light emitter to at least one of the wearer's eye; and/or the first vision zone is adapted for far vision, the wearer parameter indicates that the wearer is myopic, and during the light function adapting step a visual signal is address to the wearer when the wearer is gazing at near distance through the first vision zone; and/or the evolution of the at least one wearer parameter is checked over time and the visual profile of the wearer is adapted according to the evolution over time of the at least one wearer parameter; and/or the method further comprises a pre-calibration step during which the value of the at least one wearer parameter is determined by downloading a wear visual profile from a distant entity and/or by carrying out visual tests.

The invention further relates to a head mounted electro-optical device comprising a control unit configured to control the head mounted device function of the device and a processor adapted to implement a method according to the invention.

According to a further aspect, the invention relates to a computer program product comprising one or more stored sequences of instructions that are accessible to a processor and which, when executed by the processor, causes the processor to carry out the steps of the method according to the invention.

The invention further relates to a computer readable medium carrying one or more sequences of instructions of the computer program product according to the invention.

Furthermore, the invention relates to a program which makes a computer execute the method of the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Non limiting embodiments of the invention will now be described with reference to the accompanying drawings in which.

Figure 1:
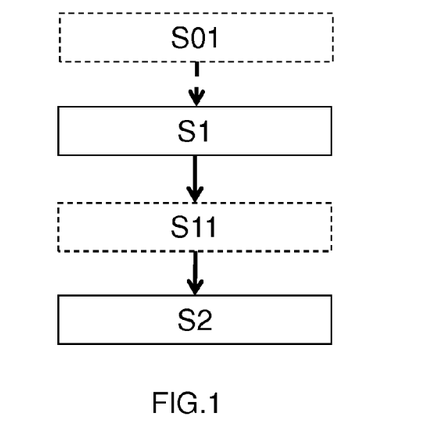
FIG. 1 is flowchart representing the steps of a method according to an embodiments of the invention.

According to an embodiment of the invention illustrated on FIG. 1, the method of controlling a head mounted electro-optical device adapted to a wearer, comprises:

a wearer visual profile parameter providing step S1, an head mounted device function adapting step S2.

During the wearer visual profile parameter providing step S1, the value of at least one wearer parameter relating to the visual profile of the wearer is provided.

In the sense of the invention, the visual profile of the wearer is to be understood as a set of parameters related to the wearer. The visual profile comprises parameters defining the vision of the wearer in a static and dynamic matter.

The visual profile includes for example, visual acuity at near, far, a prescription ophthalmic lenses, including measures of sphere, cylinder and axis for each eye of the wearer.

The visual profile of the wearer may also include parameters that are not directly related to an ophthalmic parameter depending on the desired settings of the HMD such as the colors of the wearer's eyes, the light and/or glare sensitivity or recovery of the wearer, the dark adaptation of the user, color vision of the user, visual field, binocular vision, saccadic eye movements of the wearer, fixation stability, the visuomanual coordination of the wearer, the "head/eye" movement coordination of the wearer, the gazing direction of both eyes of the wearer at a given distance vision and so forth, pupil dilation, eyelid position.

According to an embodiment of the invention, the method may comprise a pre-calibration step S01, during which the values of the wearer parameters comprised in the visual profile of the wearer are determined.

The values of the wearer parameters may be determined by downloading the wearer's visual profile from a distant entity. Typically, a distant entity may store data relating to the wearer. Among such data, some data may be identified as part of the wearer's visual profile.

During the pre-calibration step, the head mounted electro-optical device is connected to the distance entity to download the visual profile.

Visual tests may be carried out either to determine the visual profile of the wearer or in addition to the downloaded values of the wearer's visual profile so as to complete or adjust the visual profile of the wearer.

For example, the wearer may be asked to gaze at near distance target and the gazing directions of both eyes of the wearer may be determined. Such gazing directions may be used to determine the viewing distance of the wearer.

According to an embodiment of the invention, the pre-calibration step is performed by interactive series of tests to assess visual performance and evaluation on subjective preferences of the wearer.

Beforehand, the visual profile of the wearer may be entered in a data base, be segmentation based on criteria such as:

The wearer's refraction Rx

The wearer has a particular disease (menu: AMD, cataracts, retinitis pigmentosa . . . )

Age of the wearer: <45-45-70 years->70 years

Preferred type of activity: reading, video, photos . . .

Then, the pre-calibration aims at determining visual performance of the wearer based on different criteria.

This step can be carried out, for examples, on a text (recognition of letters, words), an image (pattern recognition in an image, visage recognition), a real word scene (pattern recognition on mobility). The parameters of the image processing or word processing vary depending on the media displayed, as is a text or an image.

This step may aim at identifying different visual performance required to perform on a reading task or image recognition.

The detailed examples below, may be implemented with a head mounted display device comprising a display component and a display emitter adapted to emit light to the user's eye, the light represents an image or text. An example of such head mounted display device is disclosed in WO0195027.

The images or letters used in the detailed examples may also be displayed on a distant screen or simply on paper.

EXAMPLE SEQUENCE OF TESTS

Acuity Test Visualization Letter

The acuity test aims at determining the smallest identifiable character by the wearer at a given distance. For example, this step is carried out with the image or letters vary in size according to a logarithmic progression. The subject indicates the smallest size letter read. Preferably, the letters are chosen from the so called SLOAN letters and are displayed with a contrast of 100%.

Determining the smaller letter read by the wearer via the image display device corresponds to a certain visual acuity, namely a letter size to show it to be seen and identified. The size of the letter should be optimized (the smallest comfortable) to give the reader a visual comfort and optimal field of vision. Increasing the size of the letters reduces the number of letters or image that may be displayed at once, thus making the reading not as comfortable. Therefore, determining a compromise between the size of the displayed letters and visual field provides optimal reading conditions for the wearer.

Contrast Test

The contrast test aims at determining the wearer's ability to distinguish the smallest visible contrast between a letter and real-world scene. However, it is known that the contrast threshold depends on the size of the letter. The contrast measurement is carried out using the size of the determined optimal letter in the previous step, to obtain the measurement of the fairer threshold contrast.

For example, the contrast measurement is carried out by displaying letters decreasing contrast. If the display zone is small and the letters do not fit on the display zone, this step is performed by scrolling letters. The wearer indicates the lowest perceptible contrast. The value of the contrast threshold (in %) is stored. The display process may then be adjusted according to the value of this threshold.

Test Font (about Preferences)

The test font aims at selecting a font to be displayed. Depending on the wearer, visual comfort is greater if the text is displayed in Arial or Times font for example, or in other fonts. Indeed, the visibility of the letter, the design of the letter impacts the performance of reading matter. Under certain conditions, the subject may prefer human characters and not Gothic. For example, a wearer suffering from macular degeneration related to age (AMD), rather exploits the peripheral retina that have a lower resolution than the central area of the retina areas. Therefore, affected individuals generally prefer block letters easier to identify by the peripheral zone of the human retina.

For example, selecting a font includes displaying in four separate sub-zones of the display zone, letters of the size defined in step 1, with different fonts in different quadrants (eg Arial, Times, Courier, . . . ). The wearer may then select a preferred font.

Test Space Characters (about Preferences)

The spacing test aims at determining the optimum spacing between the characters so as to facilitate the recognition of a text. In the presence of retinal pathology, the wearer is confronted with a difficulty in distinguishing letters close to each other (effect of crowding). This phenomenon is accentuated when a subject affected by retinal disease such as AMD, reads using the peripheral area of the retina.

The character spacing test comprises displaying words formed from letters of the size determined in the display of letter acuity test, with the font and the previously selected and contrast with a variable spacing, for example, a single, double and triple spacing. The subject selects the provision of letter that is most favorable.

Test Reading Acuity

The reading acuity test aims at estimating a parameter reading, as the speed of reading text.

Recognition of letters or words does not require the same vision that reading sentences performance. In a continuous reading, it is important to have a good identification of the letter (previous steps maximizing the visibility of the letter) capacity. When reading, the eyes make rapid movements exploration of the text. It is also important to have a good oculomotor control to continuously explore all the elements of the text. It is common that the subject experiences fatigue when reading, because of difficulties in effectively move the eyes, associated with muscle strain or a modification of oculomotor control in the presence of retinal pathology.

The objective of this test is then to refine the letter size to display in a sentence reading test, keeping the parameters of the letters defined above.

The reading acuity test includes, for example sentence display pre-calibrated lengths and measuring the reading speed of the subject. We start with a letter size of not more than sharp letter to give an ease of reading about. The beginning of the end of the reading and the reading is noted.

Reading speed is calculated (number of words read per minute). The size of the letters displayed is gradually reduced following a logarithmic to evaluate each reading speed. The reading speed generally decreases as the size of the displayed letters becomes too small or difficult to read. The size of the optimal letter reading is defined as the size of letters for the greater reading speed. We can also define a threshold % from which it is considered that there is a decline in reading speed.

Test Display Mode (about Preferences)

The display mode test aims at determining the optimal spatial arrangement of words, for example, from a provision in column, line, or word for word the test display mode aims. Indeed, the display mode can affect visual comfort and endurance reading of a wearer. It is possible to facilitate reading by displaying all the text in one column, or on a single line to avoid line breaks or word by word in the case of significant visual impairment.

A document displayed with a large amount of information can cause disorientation if too many items are displayed at the same time. The choice of a particular provision can gain endurance and reduce eyestrain of the wearer.

Determining the display mode for example includes the display of different display modes, respectively, columns, lines, isolated words. The wearer chooses the display mode that best suits him.

Alternatively, an algorithm can provide a display mode depending on a predetermined reading skill. For example, if the wearer needs a large letter, it is best to restructure the layout of the text line or words. The optimal display mode can be determined based on a threshold of visual acuity predetermined to activate this mode.

At the end of each test, the result is preferably stored either in the device or the wearer visual profile stored in a distance entity is updated.

Further tests such as voice activation, light and/or glare sensitivity and/or recovery test, dark adaptation test, color vision test, or an eye movement test can also be implemented.

The visual profile parameters can be also defined by measuring the wearer's behavior and the real-word scene during some activities such as reading, watching any kind of media, etc.

The visual profile parameters or wearer preferences can be manually, semi-automatically or automatically adjusted regarding the results of these tests by the wearer, an expert or an automatic software solution.

During the head mounted device function adapting step S2, the head mounted device function of the electro-optical device is adapted based on the value of the wearer parameter (s).

According to an embodiment of the invention, the method may comprise a suggestion step during which an adapted head mounted device function is suggested to the user. According to such embodiment, the adapted head mounted device function of the electro-optical device is adapted upon validation from the user of the suggested adapted head mounted device function.

According to an embodiment of the invention, the method may further comprise an environment parameter providing step S11 prior to the head mounted device function adapting step S2. During the environment parameter providing step S11, the value of at least one, for example a plurality, of parameters related to the environment of the wearer are provided.

Advantageously, the head mounted device function may be adapted according not only to wearer parameter(s) but also according to at least an environment parameter.

Such environment parameters may correspond to the light intensity of a least part of the wearer's environment, the vision distance of the wearer, the wearer's activity detection (static, mobility, media watching), the visage detection, the collision risk detection, the head mounted device status, such as the battery level, notifications, displayed contents, or any other parameter related to the environment of the wearer.

For example, when reading a text, brightness, color contrast between letters and background color, font size and distance of the text parameters may be taken into account.

During activities such as do it yourself activity or cooking, color vision, contrast and brightness parameters may be taken into account.

According to an embodiment, the head mounted device function may be switched between different predetermined head mounted device functions.

For example, if the head mounted device function relates to the opacity of a light filter, a first head mounted device function may correspond to a transmission greater than 75% and a second head mounted device function may correspond to a transmission smaller than 30%. Based on the light sensitivity of the wearer and the light intensity of the wearer's environment, the head mounted device function of the electro-optical device is switched between the first and the second head mounted device functions.

The following embodiments illustrate the configuration of the head mounted electro-optical device functions based on the visual profile of the wearer and environment parameters.

For example:

zoom settings and font size settings may be adapted based on magnification needs of the wearer, contrast enhancement may be adapted based on contrast enhancement wearer preferences and the contrast sensitivity of the wearer;

color enhancement may be adapted based on color saturation need of the wearer;

details enhancement may be adapted based on light and contrast parameters image processing may be performed based on saccadic eye movements and/or fixation stability and/or visual field of the wearer;

light and/or contrast settings and/or light transitions may be adapted according to the movements of the wearer and/or the glare and light sensitivity or recovery of the wearer and/or the eye strain of the wearer.

More particularly, according to an embodiment of the invention, the method is applied to control the filter property of a head mounted electro-optical device comprising a filter.

Such electro-optical device comprises:
- an optical lens,
- an controllable filter regarding its transmission, its reflexion and/or its absorption specifications, adapted to filter at least part of the light reflected on the optical lens or passing through the optical lens,
- a light intensity sensor adapted to determine the light intensity of at least part of the wearer's environment, and
- a control unit configured to control the specifications of the filter.

To provide an efficient control of the specifications of the filter, at least one of the wearer parameters relates to the light sensitivity of the wearer and at least one of the environment parameters relates to the light intensity of at least part of the wearer's environment.

The specifications of the filter are adapted during the head mounted device function adapting step based not only on the light intensity of the wearer's environment but also based on the light sensitivity of the wearer.

In particular, the method according to the invention may be used to improve known glare-shielding glasses.

Further wearer parameters such as the wearer's glare sensitivity and/or the wearer's eye color may be included in the visual profile of the wearer and considered when adapting the specification of the filter.

Further wearer parameters such as the dilatation of the wearer's pupil and/or the wearer's blinking frequency and/or the wearer's eyelid wrinkling or closing may be considered, for example as a sign of glare of the wearer, during the head mounted device function adapting step.

The method according to the invention may also be used to improve the head mounted electro-optical devices.

According to an embodiment, the method may be implemented in a device comprising a light emitting component. The controllable light emitter is adjustable on the light intensity and/or on the content, as the color, the display image processing or content layout.

The method further comprises, a light emitter function determining step during which at least the light intensity of the emitter is determined according at least to the light intensity of at least part of the wearer's environment and/or at least to one environment parameter relating to the head mounted electro-optical device status, as the battery level and/or the content of the displayed images, and at least a wearer parameter relating at least to the wearer's light sensitivity.

In particular, the light emitter function will be defined for minimizing the power consumption when the battery level is low.

In particular, the light emitter function will be defined for maximizing wearer comfort, content visibility, immersion, see-through visibility and/or Augmented Reality efficiency.

According to an embodiment, the method may be implemented in a device comprising further to a filter a light emitting component. The controllable filter is placed between the environment and the light emitting component and/or between the wearer and the light emitting component when the device is worn by the user.

The method further comprises, prior to the light function adapting step, a filtration specification and level determining step during which at least a filtration level corresponding to a compromise between the light intensity of the emitter and the light of the controllable filter is determined according at least to the light intensity of at least part of the wearer's environment and at least a wearer parameter relating at least to the wearer's light sensitivity.

During the light function adapting step the light function of the filter is adapted based on the filtration specification and level determined during the filtration specification and level determining step.

Both emitter and filter will be adjusted and advantageously combined.

In particular, the light emitter function will be defined for minimizing the power consumption and the light function of the filter will be defined for maximizing wearer comfort, content visibility, immersion, see-through visibility and/or Augmented Reality efficiency.

The method according to the invention may further comprises, prior to the head mounted device function adapting step, an filtration specification determining step during which a filtration specification and level corresponding to a compromise between the light intensity of the light emitter and the filtration of the controllable filter is determined according at least to the light intensity of at least part of the wearer's environment and at least a wearer parameter relating at least to the wearer's light sensitivity.

During the head mounted device function adapting step the specification and filtration level of the filter is adapted based on the filtration specification and level determined during the filtration specification and level determining step.

Advantageously, the method according to the invention allows controlling the specifications of the filter around the images displayed by the display emitter, thus increasing the contrast between the displayed image and the real-world scene. The method according to the invention may further adapt the specification of the filter in a dynamic matter. In other words, the specification of the zones of the filter around the displayed images may be specifically adapted.

Furthermore, the display device may adapt to the environment condition considering the wearer's visual profile.

The filter specifications, such as the area of filtration, the filtration level or the filtration tint, and/or the display device such as the back light level may be adjusted regarding the head mounted battery status or the displayed contents or when the eyelid are closed or if the wearer is not stable or is not looking at the display or is facing an object of interest (visage, sign . . . ), in accordance with the wearer visual profile.

In particular, the zone of the filter may be adapted to the content of the displayed images for maximizing the content visibility, as image, text or letter, and for minimizing the occlusion of the real word.

Figure 2:
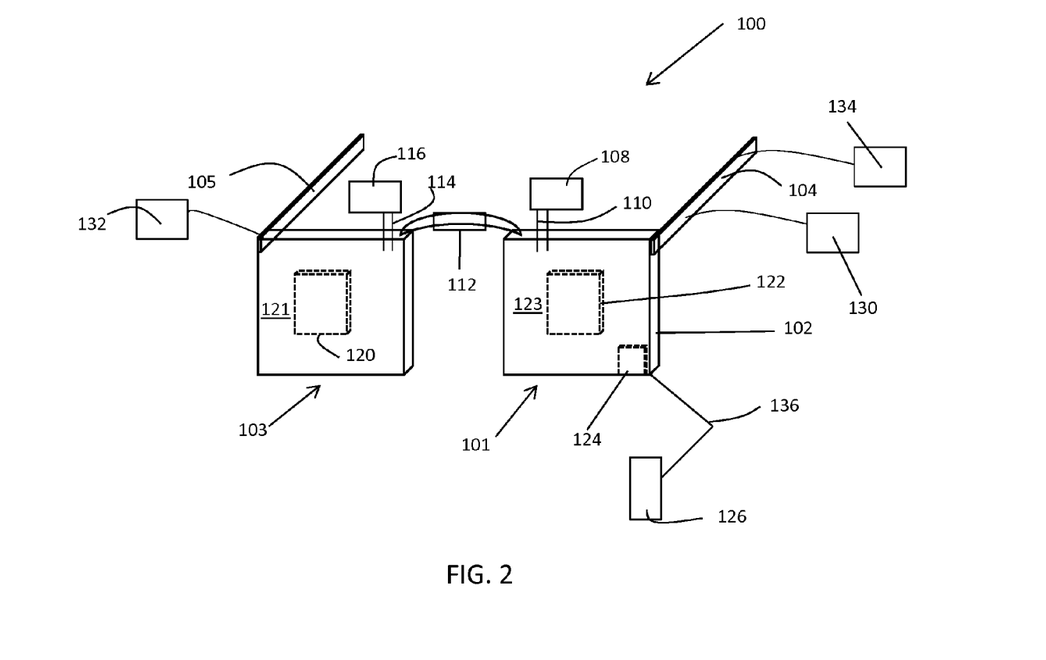
FIG. 2 represents a head mounted electro-optical device that may implement a method according to an embodiment of the invention.

FIG. 2 depicts an example implementation of a head mounted see-through electro-optical device 100.

In this example, the frame is similar to a conventional eyeglasses frame and can be worn with a similar comfort level. However, other implementations are possible, such as a face shield which is mounted to the user's head by a helmet, strap or other means. The frame includes a frame front 102 and temples 104 and 105. The frame front holds a see-through lens 101 for the user's left eye and a see-through lens 103 for the user's right eye. The left and right orientations are from the user's perspective. The left-side see-through lens 101 includes a light-transmissive opacity filter 123 and a light-transmissive optical component 122 such as a beam splitter which mixes an augmented reality image with light from the real-world scene for viewing by the left eye. An opening 124 in the opacity filter can be provided to allow an eye tracking component 126 to image the left eye, including the pupil. The opening can be, e.g., a hole in the lens 101, or a region of the lens 101 in which the opacity filter is not provided or id controlled so as to allow the eye tracking. The opacity filter can be provided in or on another light-transmissive lens material such as glass or plastic, as mentioned. Infrared light used by the eye tracking component 126 can pass through such a light-transmissive lens material.

The eye tracking component 126 can be mounted to the frame via an arm 136, in one possible approach. According to an alternative embodiment, the eye tracking component may be directly on, and inside, the front eye glass frame 102, the temple 104 or the bridge of the frame.

The right-side see-through lens 103 includes a light-transmissive opacity filter 121 and an optical component 120 such as a beam splitter which mixes an augmented reality image with light from the real-world scene for viewing by the right eye.

A right-side augmented reality emitter 116 is mounted to the frame via an arm 114, and a left-side augmented reality emitter 108 is mounted to the frame via an arm 110. An opacity filter control circuit 112 can be mounted to the bridge of the frame, and shared by the left- and right-side opacity filters.

The device comprises at least a sensor 132 for determining environment parameters and/or wearer parameters. The device further comprises processing means 134 adapted to determine based on the received the wearer parameters and the environment parameters the head mounted device function.

An electrical power source 130, for example a battery provides power to the different elements of the head mounted device.

Appropriate electrical connections can be made via conductive paths in the frame, for instance.

According to an embodiment of the invention, the method of the invention may be used to assure a more optimum use of ophthalmic lenses, in particular of ophthalmic lenses configured for different vision distances.

It has been observed that some individuals, in particular children, focus inaccurately when they observe an object which is situated at a short distance away, that is to say, in near vision conditions. Because of this focusing defect on the part of a myopic child which is corrected for his far vision, the image of an object close by is also formed behind his retina, even in the foveal area.

To slow down myopia progression which is due to this focusing defect, it is known to use a myopia-correcting lens which is of the discontinuous or progressive multifocal ophthalmic lens type. An example of such progressive multifocal ophthalmic lens is disclosed in U.S. Pat. No. 6,343,861.

Such a multifocal ophthalmic lens comprises a far vision area, in which the optical power of the lens is adapted to correct the myopia of the wearer when observing far/distant objects, a near vision area, in which the myopia correction is reduced, and an intermediate area which is situated between the far vision and near vision areas, and in which the optical power of the lens varies continually. Such multifocal ophthalmic lenses are adapted for the foveal vision of the weaver.

It has been observed that the efficiency of such multifocal ophthalmic lens and more generally the efficiency of myopia control lenses, is highly variable from one wearer to another.

One reason of such high variance is the improper use by the wearer of such myopia control lenses.

Indeed, as most myopic wearers of those lenses are not presbyopic, they do not require any change in power to clearly see near objects and can therefore use any part of a multifocal ophthalmic lens to read or write.

It has been observed that some wearers do not use the proper part of the myopia control lens, in particular when carrying out near vision tasks, thus reducing the benefic effect of such myopia control lens.

In addition some early adopters or $1^{st}$ user of presbyopia corrective lenses may have some difficulties to find the proper part of presbyopia lens to use regarding the object distance.

Therefore, there is a need to provide a method that helps the user use properly the myopia control lenses or presbyopia corrective lenses so as to increase the efficiency of such lenses.

A goal of the present invention is to provide such a method.

In accordance with an aspect of the invention the method of the invention is implemented for a head mounted see-through electro-optical device comprising:
  an optical lens mounted to a frame worn by the wearer, the optical lens comprises at least a first and a second distinct vision zone, the first vision zone being adapted to a first distance vision, and the second vision zone being adapted for a second distance vision different from the first distance vision, and
  an eye tracking component adapted to determine the gazing direction of the wearer.

According to such aspect of the invention the at least one wearer parameter relates to the wearer's ophthalmic prescription, at least one visual parameter relates to the viewing distance of the wearer and a further visual parameter relates to the gazing direction of the wearer.

During the head mounted device function adapting step, the head mounted device function is adapted so as to address a visual signal to the wearer when based on the wearer's ophthalmic prescription; the gazing direction does not correspond to the viewing distance. In other words, a visual signal is address to the wearer when the wearer has an improper use of the device.

Having a visual signal helps the wearer use most efficiently the pair of ophthalmic lenses. In particular makes the wearer gaze through the correct vision zone.

The viewing distance of the wearer may be determined by comparing the gazing directions of both eyes of the wearer. Indeed, the closer from the wearer the gazing directions of both eyes cross, the smaller is the viewing distance. According to an embodiment of the invention, the gazing directions of both eyes may be compared to a pre-determined value determined during the pre-calibration step to correspond to reading vision so as to determine when the wearer is reading.

The gazing direction may also be used to determine the vision zone used by the wearer.

The visual signal address to the wearer may comprise a change of color and/or of opacity of at least part of the see-through electro-optical device and/or displaying an image to the wearer using an emitting component adapted to emit light to at least one of the wearer's eye.

In particular, the visual signal can be combined with audio signal or voice message for quickly drive the wearer to the correct vision zone.

Advantageously, the method of the invention is used to help reduce myopia progression of the wearer or to help efficient use of any multifocal lenses such as presbyopia lenses. For example, the first vision zone is adapted for far vision, the wearer parameter indicates that the wearer is myopic, and during the head mounted device function adapting step a visual signal is address to the wearer when the wearer is gazing at near distance through the first vision zone.

Although the above embodiment has been described in detail for myopia control lens, the invention is not limited to such myopia control lens, in particular, the invention may be used for presbyopia control.

Furthermore, the invention also relates to a method, wherein the head mounted electro-optical device is a see-through head mounted electro-optical device comprising:
- an optical lens mounted to a frame worn by the wearer, the optical lens being a monofocal lens adapted for a given distance vision,
- an eye tracking component adapted to determine the gazing direction of the wearer, and wherein
the at least one wearer parameter relates to the wearer's ophthalmic prescription,
during the environment parameter providing step, at least one environment parameter relating to the viewing distance of the wearer is provided, and,
during the head mounted device function adapting step, the head mounted device function is adapted so as to address a visual signal to the wearer when based on the wearer's ophthalmic prescription the viewing distance is incorrect, either too short or too big.

The environment parameter provided during the environment providing step may be used to detect an environment that may increase either the myopia or the presbyopia of the user and upon such detection a visual signal is address to the wearer.

The invention further relates to a head mounted see-through electro-optical device comprising a control unit configured to control the head mounted device function of the device and a processor adapted to implement a method according to the invention.

According to an embodiment of the invention, the head mounted electro-optical device comprises communication means adapted to communicate with a distance entity. As indicated previously, the wearer visual profile may be stored in such distant entity. The head mounted electro-optical device may send to the distance entity wearer parameter(s) and/or environment parameter(s). The distant entity based on the wearer parameter(s) and/or environment parameter(s) may determine the head mounted device function to be applied and sends it to a controller comprised in the head mounted electro-optical device. The determined head mounted device function may then be applied by the head mounted device. Advantageously, all the processing means are centralized and the head mounted device does not need to be carried on the head mounted device.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method of controlling a head mounted electro-optical device adapted to a wearer, wherein the head mounted electro-optical device comprises: an optical lens, at least a controllable light filter adapted to filter at least part of the light passing through the optical lens or reflected on the optical lens, a control unit configured to control the controllable light filter with the method, the method comprising:
   performing a wearer visual profile parameter providing step that includes obtaining a value of at least one wearer parameter related to a visual profile of the wearer;
   performing an environment parameter providing step that includes obtaining a value of at least one environment parameter relating to an environment of the wearer;
   performing a head mounted device function adapting step that includes modifying at least one head mounted device setting of the head mounted electro-optical device based on the value of the at least one wearer parameter and on the value of at least one environment parameter;
   periodically and automatically updating the value of the at least one wearer parameter;
   modifying the visual profile of the wearer according to the updated at least one wearer parameter; and
   performing a second head mounted device function adapting step that includes modifying at least one head mounted device setting of the head mounted electro-optical device based on the updated value of the at least one wearer parameter and on the value of at least one environment parameter.

2. The method according to claim 1 wherein at least one environment parameter relates to a status of the head mounted electro-optical device.

3. The method according to claim 1, wherein the head mounted device function adapting step includes switching between at least two predetermined head mounted device settings.

4. The method according to claim 1, wherein the head mounted electro-optical device comprises:
   at least a light intensity sensor adapted to determine a light intensity of at least part of the wearer's environment, wherein the at least one wearer parameter relates to at least a light sensitivity of the wearer, the at least one environment parameter relates to at least the light intensity of at least part of the wearer's environment and wherein the head mounted device function adapting step further includes modifying at least an opacity of the controllable light filter.

5. The method according to claim 1, wherein the at least one wearer parameter relates to at least one of the wearer's glare sensitivity, the wearer's eye color, the wearer's preference, the dilatation of the wearer's pupil, the wearer's blinking frequency, and the wearer's squinting.

6. The method according to claim 4, wherein the head mounted electro-optical device further comprises a light emitting component, the controllable light filter being placed between the environment and the light emitting component or between the wearer and the light emitting component when the device is worn by the wearer, and the method further comprises performing, prior to a light function adapting step, a filtration specification and level determining step that includes determining at least a filtration specification and level corresponding to a compromise between the light intensity of the light emitting component and the light of the controllable light filter according at least to the light intensity of at least part of the wearer's environment and at least a wearer parameter relating at least to the wearer's light sensitivity, and during the head mounted device function adapting step, modifying a light function of the controllable filter based on the filtration specification and level.

7. The method according to claim 6, wherein the light emitting component comprises a display emitter adapted to emit light to the wearer's eye, the light representing at least one of an image and a letter, and wherein the filtration specification and level describe a static or dynamic pattern having a higher or lower filtration level within the surrounding of the display emitted light than the display area or some sub-part of the display area.

8. The method according to claim 6, wherein the head mounted electro-optical device is a see-through head mounted electro-optical device comprising:

an optical lens mounted to a frame worn by the wearer, the optical lens comprises at least a first and a second distinct vision zone, the first vision zone being adapted to a first distance vision, and the second vision zone being adapted for a second distance vision different from the first distance vision, an eye tracking component adapted to determine a gazing direction of the wearer, and wherein during the visual environment parameter providing step, at least one visual parameter relating to the viewing distance of the wearer is provided and at least one visual parameter relating to the gazing direction of the wearer is provided, during the light function adapting step, modifying the light to address a visual signal to the wearer when the gazing direction does not correspond to the viewing distance.

9. The method according to claim 8, wherein the viewing distance of the wearer is determined by comparing the gazing directions of both eyes of the wearer.

10. The method according to claim 8, wherein the visual signal address to the wearer comprises a change of color and/or of opacity of at least part of the head mounted electro-optical device and/or displaying a light to the wearer using a light emitter to at least one of the wearer's eye.

11. The method according to claim 8, wherein the first vision zone is adapted for far vision, the wearer parameter indicates that the wearer is myopic, and during the light function adapting step a visual signal is address to the wearer when the wearer is gazing at near distance through the first vision zone.

12. The method according to claim 1, wherein the method further comprises performing a pre-calibration step during which the value of the at least one wearer parameter is determined by performing one of downloading a wear visual profile from a distant entity or by carrying out visual tests.

13. A head mounted see-through electro-optical device including an optical lens, at least a controllable light filter adapted to filter at least part of the light passing through the optical lens or reflected on the optical lens, a control unit configured to control a light function of the device, and a processor adapted to implement a method comprising:

performing a wearer visual profile parameter providing step that includes obtaining a value of at least one wearer parameter related to a visual profile of the wearer;

performing an environment parameter providing step that includes obtaining a value of at least one environment parameter relating to an environment of the wearer;

performing a head mounted device function adapting step that includes modifying at least one head mounted device setting of the head mounted electro-optical device based on the value of the at least one wearer parameter and on the value of at least one environment parameter;

periodically and automatically updating the value of the at least one wearer parameter;

modifying the visual profile of the wearer according to the updated at least one wearer parameter; and performing a second head mounted device function adapting step that includes modifying at least one head mounted device setting of the head-mounted electro-optical device based on the updated value of the at least one wearer parameter and on the value of at least one environment parameter.

* * * * *